(12) United States Patent
Brazenor

(10) Patent No.: US 8,574,298 B2
(45) Date of Patent: Nov. 5, 2013

(54) SPINAL IMPLANT

(75) Inventor: Graeme Brazenor, Richmond (AU)

(73) Assignee: Edinowa Pty Ltd., Richmond (AU)

( * ) Notice: Subject to any disclaimer, the term of this patent is extended or adjusted under 35 U.S.C. 154(b) by 1747 days.

(21) Appl. No.: 11/017,833

(22) Filed: Dec. 22, 2004

(65) Prior Publication Data

US 2005/0113922 A1 May 26, 2005

Related U.S. Application Data

(63) Continuation of application No. PCT/AU03/00932, filed on Jul. 21, 2003.

(30) Foreign Application Priority Data

Jul. 26, 2002 (AU) ................................ 2002950443

(51) Int. Cl.
*A61F 2/44* (2006.01)

(52) U.S. Cl.
USPC ...................... 623/17.15; 623/17.11; 623/908

(58) Field of Classification Search
USPC .......................... 606/246, 251, 254, 255, 279;
623/17.15, 17.12, 17.13, 17.14, 908
See application file for complete search history.

(56) References Cited

U.S. PATENT DOCUMENTS

| | | | |
|---|---|---|---|
| 4,369,769 A | 1/1983 | Edwards | |
| 4,445,513 A | 5/1984 | Ulrich et al. | |
| 5,242,446 A * | 9/1993 | Steffee et al. | 606/254 |
| 5,534,030 A * | 7/1996 | Navarro et al. | 623/17.15 |
| 5,704,936 A * | 1/1998 | Mazel | 606/255 |
| 5,776,197 A * | 7/1998 | Rabbe et al. | 623/17.15 |
| 6,294,187 B1 * | 9/2001 | Boyce et al. | 424/422 |
| 6,761,719 B2 * | 7/2004 | Justis et al. | 606/255 |
| 2002/0010473 A1* | 1/2002 | Lin | 606/99 |
| 2002/0087159 A1* | 7/2002 | Thomas | 606/61 |

FOREIGN PATENT DOCUMENTS

| | | |
|---|---|---|
| DE | 198 56 013 A1 | 6/2000 |
| EP | 0 188 954 B1 | 7/1986 |
| FR | 2 636 227 A1 | 3/1990 |
| SU | 1470289 A1 | 4/1989 |
| WO | WO-00/33752 A1 | 6/2000 |

* cited by examiner

*Primary Examiner* — Brian E. Pellegrino
(74) *Attorney, Agent, or Firm* — Birch, Stewart, Kolasch & Birch, LLP

(57) ABSTRACT

A spinal implant is provided for retaining spinal elements in a desired spatial relationship. It includes a tensioning member positionable along the spinal column of a patient to match the contour thereof. A pair of buttress members are located each on one of the ends of the tensioning member, at least one of the buttress members being slidable on the tensioning member so that the distance between the buttress members may be adjusted.

14 Claims, 4 Drawing Sheets

SPINAL IMPLANT

This application is a Continuation under 35 U.S.C. §120 of PCT International Application No. PCT/AU2003/000932 filed on Jul. 21, 2003, which claims priority under 35 U.S.C §119(a) to Patent Application No. 2002950443 filed in Australia on Jul. 26, 2002.

BACKGROUND OF THE INVENTION

1. Technical Field

The present invention relates to apparatus and a method for retaining vertebrae of a spinal column of a patient in a desired spatial relationship. The invention will be described with particular reference to use as an anterior cervical spinal implant although it will be appreciated that the invention has wider application as will appear from the description that follows.

Cervical spinal implants are used to maintain a desired spatial relationship of cervical vertebrae in patients suffering from a number of conditions such as degenerative disc disease, trauma including fractures, tumours, deformity or failed previous fusions.

2. Description of the Prior Art

The usual procedure for decompressing and stabilising cervical spine over several segments involves the introduction of a long bone graft, harvested either from iliac crest or fibula, and stabilised with a rigid elongate perforated plate, screwed to the vertebra above and below the graft.

Whilst this usual procedure has provided satisfactory results in the past, there are numerous problems associated with it. First, it is difficult to introduce the bone graft into the vertebral defect under sufficient tension for the bone graft to be retained in a stable fashion. Secondly, the implanted plates sometimes work loose because the screws at either end are subjected to pull-out forces akin to those of a nail gripped by a claw hammer. Thirdly, because the screws are driven in from directly anteriorly, the vertical extent of the operative exposure is greater than the vertical extent of the vertebral defect, increasing the time, complexity and hazard of the procedure. Finally, the harvesting of the bone graft from iliac crest or leg is in itself a traumatic procedure and greatly adds to the patient's postoperative pain and disability, and prolongs rehabilitation.

It is an object of the invention to provide a spinal implant which provides stability to the spine, without the need for harvesting of a large bone graft from another part of the patient's body.

SUMMARY OF THE INVENTION

According to the invention there is provided an apparatus to retain in a desired spatial relationship, spaced apart portions of elements such as spinal elements, the apparatus including
- a pair of spaced apart buttress members,
- a tensioning member adjustably connected with at least one of said buttress members, and
- retaining means to hold said tensioning member in a fixed position in relation to said buttress members, whereby said buttress members may be connected to the spaced apart portions of the elements, said tensioning member placed in relation to said buttress members such that said spaced apart portions are in a desired relative position and said retaining means is used to hold the apparatus in that position.

In one embodiment of the invention there is provided apparatus for use in retaining spinal elements in desired spatial relationship, said apparatus comprising:
- a tensioning member positionable along the spinal column and having a first end, a second end and a longitudinal axis extending therebetween;
- first and second buttress members located on said first and second ends of said tensioning member, each buttress member including an abutment surface, and wherein at least one of said buttress members includes a passage to receive one of said first or second ends of said tensioning member wherein said tensioning member is slideably moveable in said passage, and retaining means to secure said tensioning member and said buttress in fixed relative position; and
- wherein a line coaxial with the axis of said tensioning member at said first and second ends and extending from said tensioning member beyond said first and second ends intersects with said abutment surface.

The tensioning member may be a rod which is circular in transverse section as is commonly used in the art although other shapes or arrangements of tensioning member may be equally suitable. For example, the tensioning member may be square, rectangular "C" or "I" shaped in transverse section. The axis or lengthwise shape of the tensioning member may be straight or curved or arcuate. More preferably it is straight at each end but includes an arcuate section in a medial region. The tensioning member may be made of metal such as stainless steel or titanium alloy for example, severable to the desired length and may be deformable longitudinally to a shape to suit the cervical curvature of the patient. Those skilled will appreciate that the material of which the tensioning member is made should be deformable to a shape that will be retained under the conditions in which it is used. Thus, the shape of the arcuate section of the tensioning member may be chosen to achieve the desired cervical curvature when the apparatus is implanted. The exact configuration of the axis and length of the tensioning member may be determined and adopted intraoperatively.

Preferably, the axis of the tensioning member in the regions where its ends insert into the passages are substantially perpendicular to the plane of each abutment surface. In this arrangement load applied to the abutment surfaces of the buttresses or distension force applied by the outward facing abutment surfaces is borne substantially along the axis of the tensioning member.

The buttress may be of any suitable form including a disc shaped or cylindrical member to provide a buttress surface. At least one of the buttress members includes a longitudinally extending recess for receiving an end of the tensioning member and include a laterally extending recess in which a grub-screw may be inserted to hold the end of the tensioning member. Other fastening means of adjustably fastening the tensioning member to the buttress member may be provided as will be appreciated by those skilled in the art.

The buttress members may be provided additionally with holding means if desired. These may take the form of one or more integral spikes to assist in holding the buttress to the vertebral contact surface. In addition, the abutment surface may include means to facilitate osseous integration therewith. In one embodiment the abutment surface may include a porous coating comprising one or more layers of spherical particles. In another embodiment the abutment surface may include a recessed region into which a bone growth promoting compound is applied.

Preferably, each buttress includes a passage which opens from the body away from the abutment surface and into which an end of the tensioning member is inserted. Preferably the passage terminates in said body proximate said abutment surface, so that the end of the tensioning member does not pass through or project from the buttress beyond the abutment surface, i.e. passages are blind passages and thus the ends of the tensioning member are contained within the passages.

Means are provided to secure the tensioning member and each buttress in fixed relative position. In a preferred embodiment this comprises a screw in the body of the buttress which can be tightened against part of the tensioning member which is inserted into the passage so that the tensioning member is pressed against the wall of the passage and is held in frictional engagement therewith. Alternatively, other methods of selectively securing the tensioning member and each buttress in fixed relative position may be provided.

In another embodiment of the invention, the tensioning member is integrally molded with one buttress member or otherwise fixed thereto.

In another aspect of the present invention there is provided a buttress for use in conjunction with a tensioning member in a spinal column retaining apparatus for retaining spinal elements in a desired spatial relationship, the buttress comprising:

a body having a first end with an abutment surface, and a passage in said body opening at a second end and extending through said body towards said abutment surface, wherein said passage is adapted to receive an end of a tensioning member; and means to secure said buttress with a tensioning member in said passage.

Preferably the buttress will include one or more of the preferred features previously described.

In yet another embodiment of the invention there is provided a method for retaining vertebra of a spinal column in a desired spatial relationship, the method comprising:

(a) excising portions of upper and lower vertebrae to form contact surfaces;
(b) providing a spinal implant as herein described.
(c) installing said implant between said upper and lower vertebrae by placing said abutment surfaces in contact with said contact surfaces.
(d) distracting said spinal column to adopt the desired spatial relationship of the vertebrae.
(e) sliding at least one of said buttresses apart along said tensioning member such that said abutment surfaces maintain contact with said contact surfaces.
(f) applying said retaining means to secure said buttresses to said tensioning member, to maintain said vertebrae in desired spatial relationship.

BRIEF DESCRIPTION OF THE DRAWINGS

The foregoing and other features of the present invention will become more apparent to one skilled in the art upon reading the following description with reference to the accompanying drawings, wherein.

DESCRIPTION OF PREFERRED EMBODIMENTS

The embodiments of the invention shown are given for illustrative purposes only and should not be taken as limiting the scope of the present invention.

Figure 1:
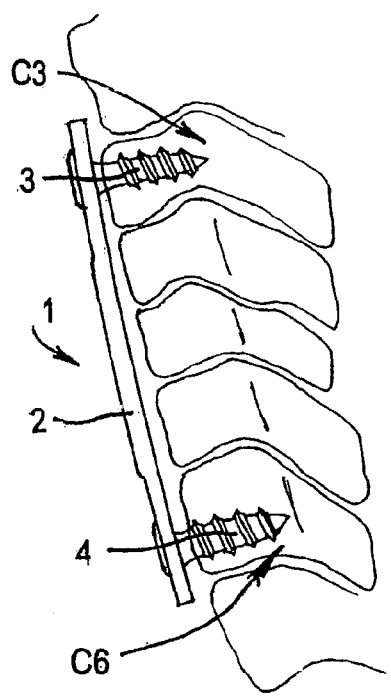
FIG. 1 is a lateral view of a cervical spine with a spinal implant of the prior art.

FIG. 1 shows typical prior art apparatus used in cervical spinal fusion surgery. Implant 1 consists of a plate 2 which is fixed to cervical vertebrae C3 to C6 by bone screws 3 and 4 respectively.

Figure 2:
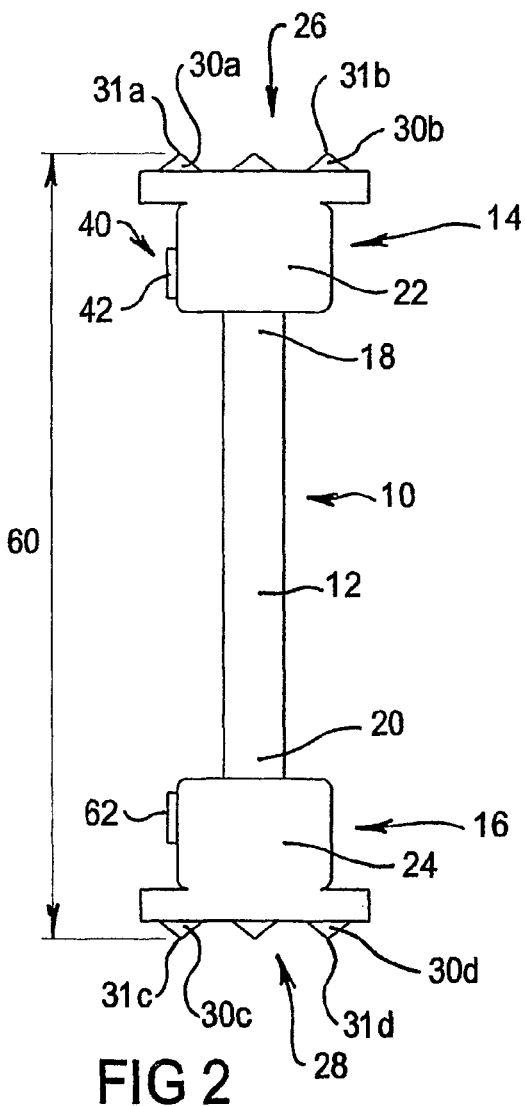
FIG. 2 is a side view of an apparatus constructed in accordance with the present invention.

In FIG. 2, spinal implant 10 consists of a rod 12, and an upper buttress 14 and a lower buttress 16. Rod 12 has a first end 18 which is inserted into a bore in upper buttress 14 and a second end 20 which is inserted into a bore in lower buttress 16.

The required length of rod 12 may be determined by the surgeon during surgery after measurement of the cervical vertebrae and calculation of the length required to keep the vertebrae in a desired spatial arrangement. The rod 12 may be cut to the desired length and bent using equipment known in the art.

Each buttress 14 and 16 respectively comprises a body 22 and 24 each having an abutment surface 26 and 28. Abutment surfaces 26 and 28 include spikes shown typically as 30a, 30b, 30c and 30d which are spaced apart and extend outwardly from the abutment surfaces 26 and 28. In the embodiment shown the spikes 30a to 30d are substantially conical and terminate in points 31a to 31d. In use the spike are pressed into surfaces exposed by excision of bone from the upper and lower vertebrae to which the implant is to be attached. The spikes 30a to 30d assist to hold the buttresses 14 and 16 in position against the vertebrae.

Figure 3:
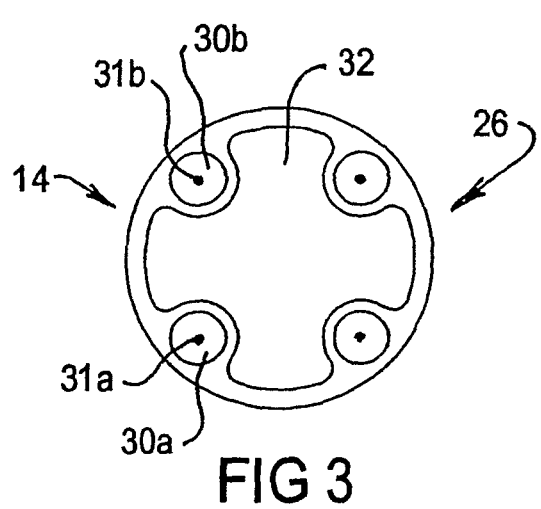
FIG. 3 is a top plan view of a typical buttress of the present invention, being the upper buttress shown in FIG. 2.
Figure 4:
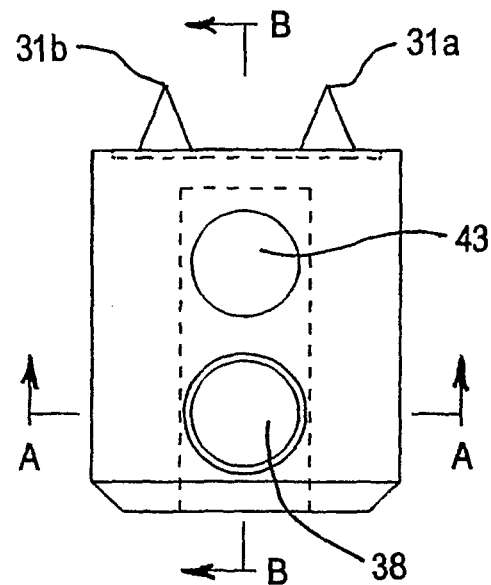
FIG. 4 is a side elevation of the buttress shown in FIG. 3.

Abutment surfaces 26 and 28 may provide bonding surfaces 32 (shown more clearly in FIG. 3) adapted to promote bony fusion of the vertebrae to the bonding surfaces 32. It should be noted that the numbering used in reference to FIGS. 3, 4, 5 and 6 applies equally to lower buttress 16. The bonding surface 32 is preferably a porous coating formed from one or more layer of spherical particles or beads such as titanium which are fused to or otherwise fixed to the abutment surfaces 26 and 28 in a manner known in the art. The coating is firmly adhered to the buttress so that it resists removal by abrasion and such that the bonding strength between the coating and the buttress is greater than the bond strength between the coating and bone to which it grafts.

Alternatively, the bonding surfaces may be etched or roughened. In another embodiment (not shown) at least a portion of the abutment surface may include a recess into which a bone growth promoting compound or putty is applied so that osseous integration of the buttress to the vertebra which it abuts is enhanced. It will be appreciated that any other form of surface treatment that promotes grafting of bone to the abutment surfaces may be suitable.

Figure 5:
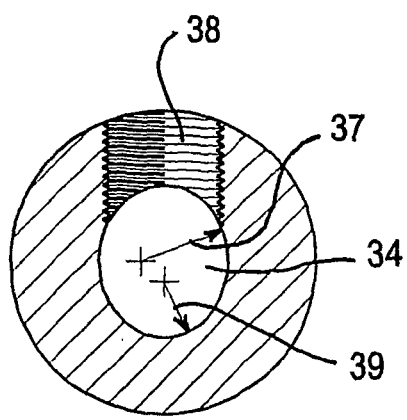
FIG. 5 is a transverse section of the buttress of FIG. 4 along the line AA.
Figure 6:
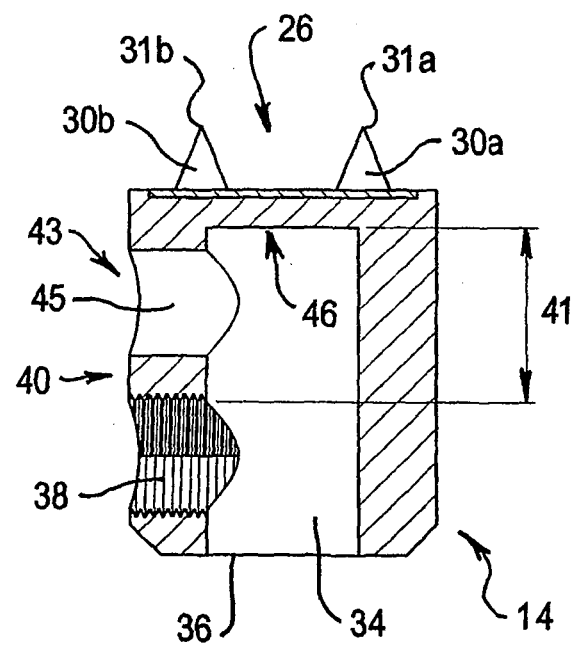
FIG. 6 is a transverse section of the buttress of FIG. 4 along the line BB.

Buttresses 14 and 16 have a body 22 and 24 defining a bore 34 (see FIG. 6) into which an end 18 of rod 12 may be inserted. Bore 34 has an opening 36 at the opposite end of the body 22 to the abutment surface 26. The bore 34 is a blind bore with bore end 46 so that the end 18 of rod 12 inserted into the bore 34 does not protrude from the abutment end of the body 22. As shown in FIG. 5, the bore 34 is preferably elliptical or oval shaped in transverse section when the rod 12 is substantially circular in transverse section. Bore 34 has a first radius 37 which is greater than the radius of rod 12 so that buttress 14 can easily be moved axially along rod 12 when rod 12 is inserted in bore 34. Second radius 39 is approximately equal to or slightly less than the radius of rod 12. The elliptical shape of bore 34 in conjunction with rod 12 may be of compatible configuration to that used in the ISOLA spinal implant system. ISOLA is a trade mark of Acromed Corporation, although it may equally be designed to be compatible with other spinal implant hardware systems.

Body 22 also includes a threaded lateral bore 38 which extends from a side 40 of body 22 and intersects with bore 34. A grubscrew 42 as shown in FIG. 1 may be inserted into threaded bore 38 and screwed until it bears against rod 12 and presses it against surface 44. Until grubscrew 42 has been tightened against rod 12, the rod 12 and buttress 14 are able to slide relative to each other until the tip (not shown) of rod 12 abuts bore end 46 of buttress 14. In this arrangement rod 12 is able to move in the portion of the bore 38 defined by first radius 37. When grubscrew 42 is tightened to the desired torque, rod 12 is forced into the portion of bore 38 defined by second radius 39 and is thus securely clamped so that the rod and buttress 14 are maintained in fixed position relative to each other.

The length 41 of the bore 34 between the edge of threaded bore 38 and bore end 46 provides the degree to which buttress 14 can be distracted from rod 12, the importance of which will become apparent from the description below. Body 22 also includes a lateral window opening 43 which is preferably positioned adjacent threaded bore 38 and on the same side of body 22, although it may be positioned elsewhere on body 22 in certain embodiments. The window opening may consist of a bore which extends from side 40 through body 22 and opens in to bore 34 between bore end 46 and the edge of threaded bore 38. Window 43 allows the surgeon to see the degree to which rod 12 has been retracted along bore 34 by viewing the end of rod 12 in bore 34. As is apparent from FIGS. 5 and 6, bore 34 has a blind end 46 and inner walls along the length of the bore are closed except for the lateral threaded bore 38 and the lateral window opening 43. Accordingly, the bore 34 opens from an end of the buttress member 14 opposite from the abutment surface 26, and terminates inside said buttress member 14 to receive an end 18 of said tensioning member 12. Except for the lateral threaded bore 38 and the lateral window 43, the inner wall of bore 34 completely surrounds an outer peripheral wall of the end 18 of rod 12.

Figure 7:
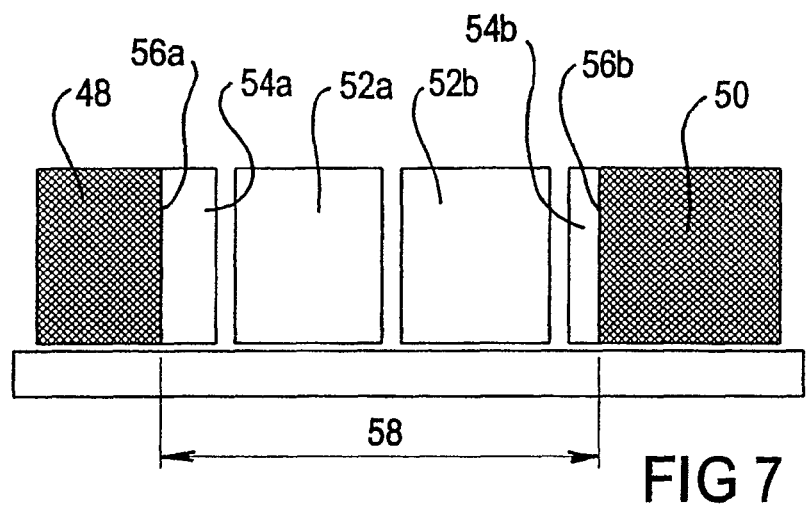
FIG. 7 is a schematic drawing of a portion of spinal column showing excision of vertebrae in preparation for implantation of apparatus of the present invention.
Figure 8:
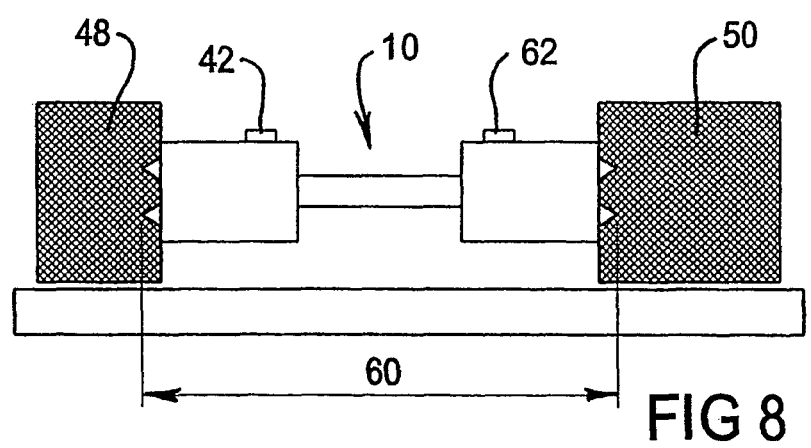
FIG. 8 is a schematic drawing of the portion of spinal column of FIG. 7 with an implant of FIG. 2 in position.
Figure 9:
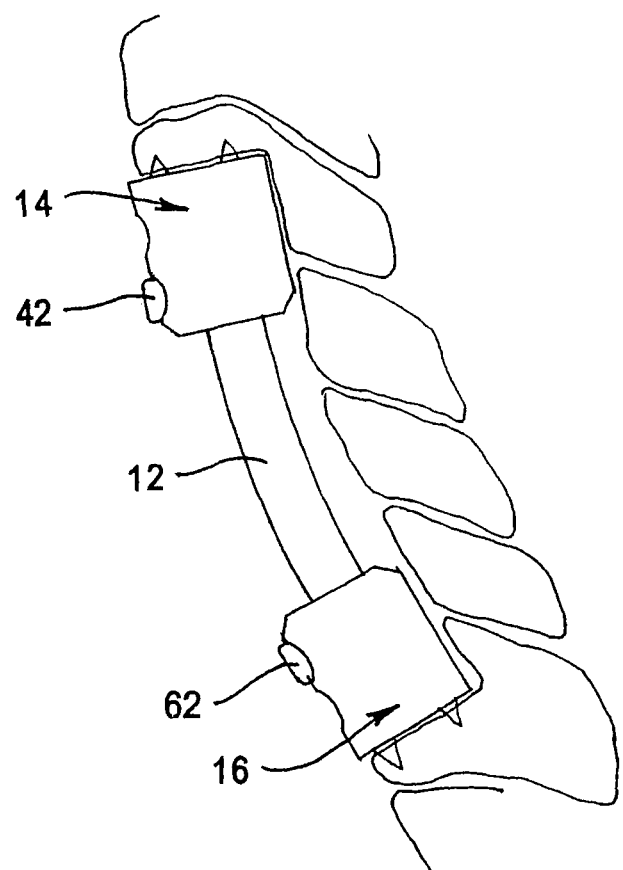
FIG. 9 is a side elevation of a cervical spine with a spinal implant of FIG. 2 installed to retain vertebrae in a desired spatial relationship.

The spinal implant 10 may be installed on the spinal column of a patient in the following manner shown with schematic representations in FIG. 7 and FIG. 8. This installation procedure is described for fixation of the anterior cervical spine. First, the upper vertebra 48 and lower vertebra 50 between which the spinal implant is to extend are selected and portions 52a and 52b (shown in ghost lines) of the vertebrae between those two vertebrae 48 and 50 are excised using surgical techniques known in the art. Portions 54a and 54b of vertebrae 48 and 50 are also excised to form contact surfaces 56a and 56b which are substantially planar, and the planes of surfaces 56a and 56b generally face each other.

The distance 58 between prepared vertebral surfaces 56a and 56b are measured for example, using callipers while no distracting force is applied to the patient's spinal column. The desired length of rod 12 is then calculated such that the length 60 of the spinal implant 10 when the tips of rod 12 are fully inserted into bores of buttresses 14 and 16 and abut the bore ends 46 of the buttresses i.e. the buttress is in a fully compressed arrangement, is substantially equal to or a few millimetres slightly greater than distance 58. Rod 12 is then cut to the calculated length from a stock length of rod as will be known in the art. Rod 12 may be bent with tools known in the art to a curvature required to achieve the necessary spatial relationship of the vertebrae.

Grubscrews 42 and 62 are inserted into the threaded bore 38 of each buttress 14 and 16 respectively, but are not screwed in to such an extent that they will protrude into bore 34. Buttresses 14 and 16 are then slid over the ends 18 and 20 of rod 12 until the ends of rod 12 come into contact with bore ends 46, i.e. the implant is assembled into its fully compressed arrangement. Screws 42 and 62 may be tightened slightly against rod 12 although only so much as to hold the assembled implant loosely together so it does not disassemble when being handled by the surgeon.

The implant is then lowered into the trench created by the surgeon with grubscrews 42 and 62 accessible for tightening. A slight distracting force may be applied to the patient's spine to increase the distance 58 so that the implant can be positioned between surfaces 56a and 56b. Points 30a, 30b, 30c and 30d are brought into contact with prepared vertebral surfaces 56a and 56b and may be pressed slightly into vertebrae 48 and 50 at those surfaces. Optionally, each buttress 14 and 16 may be hammered slightly along the axis of rod 12 so that point 30a to 30d embed in the vertebrae 48 and 50 below surfaces 56a and 56b. The slight distracting force can then be released.

A full distracting force is then applied to the patient's spinal column which increases the distance 58 between surfaces 56a and 56b once more, but this time to the extent required by the surgeon to adopt the desired spatial relationship of the patient's spinal column. Buttresses 14 and 16 are maintained in contact with distracted against surfaces 56a and 56b. This distraction causes rod 12 to retract along bores 34 but preferably not to such an extent that the end of rod 12 passes threaded bore 38. The surgeon can view the extent to which rod 12 has retracted along bore 34 through window 43. Grubscrew 42 is then tightened to the required torque to ensure that the rod 12 and buttress 14 is firmly secured together and the procedure is repeated for screws 62 and buttress 16. The distraction force is then released from the patient's spinal column so that the spinal implant 10 retains the spinal elements in the desired spatial relationship. Spikes 30a to 30d may further imbed to a small extent once muscular tension of the patient's neck returns although this will not be to such a degree as to alter the spatial relationship to any significant degree.

It has been found that by use of the present invention, a patient can be mobilized the day following surgery without the need for external orthoses. Osseous integration with the bonding surface takes place over time but, if care is taken, is not necessary for the immediate proper functioning of the implant.

This compares with a substantial period of immobilisation using currently available apparatus.

The components described above may be made from any desired materials known in the art which exhibit the required strength, longevity for permanent implantation and which do not cause the body to establish a rejection reaction. For example, the rod may be made from stainless steel or other suitable implantable metal alloys. The buttresses may be made from implant grades of titanium alloys.

The invention has been shown to provide a significant advance in surgical procedure. By use of the spinal implant in accordance with the invention, the need to harvest a large bone graft from another part of the patient's body is avoided. The vertical extent of the surgical field in the neck need not be significantly greater than the length of the vertebral defect. There is a greater ability to customise the implant during surgery. It has been found that by use of the invention, recovery time is reduced while a high degree of permanent strength and rigidity is provided.

It will be appreciated that various changes, modifications and alterations in the teaching of the invention described herein may be contemplated by those skilled in the art without departing from the ambit of the present invention as defined in the claims hereafter.

The invention claimed is:

1. Apparatus for use in retaining spinal elements of a spinal column of a patient in desired spatial relationship, said apparatus being locatable in a position where vertebral bone has been excised from the spinal column and comprising:
    a tensioning member positionable along the spinal column and having a first end, a second end, and a longitudinal axis extending therebetween;
    first and second buttress members located on said first and second ends of said tensioning member, each of the buttress members including an abutment surface, and wherein at least one of said buttress members includes a bore which opens from an end of the buttress member opposite from the abutment surface, and terminates at a closed inner end surface inside said buttress member, the bore being adapted to receive and completely surround one of said first or second ends of said tensioning member received in the bore,
    wherein the bore is formed along a central axis of the at least one buttress member,
    wherein the one of said first or second ends of said tensioning member is slideably moveable in said bore, and
    wherein when the one of said first and second ends of said tensioning member is contained within said bore, the closed inner end surface prevents the end of the tensioning member from projecting beyond the closed inner end surface;
    the apparatus further comprising
    a retainer which is adapted to secure the one of said first and second ends of said tensioning member and said buttress members in different fixed positions with respect to each other; and
    wherein a line coaxial with an axis of said tensioning member at said first and second ends, and extending from said tensioning member beyond said first and second ends, intersects with said abutment surfaces,
    wherein said tensioning member is a member which is deformable to a curved-shape to substantially match a contour of a cervical spine of the patient, and
    when the apparatus is adapted to be located in the position where the vertebral bone has been excised, and the abutment surfaces of the first and second buttress members are adapted to abut, respectively, against the spinal element adjacent thereto, the line coaxially extending beyond each of the first and second ends of said tensioning member is adapted to align, respectively, in an axial direction of the adjacent spinal element,
    wherein the apparatus is adapted to exert a force in the axial direction of each of the adjacent spinal elements.

2. An apparatus, as claimed in claim 1, wherein said tensioning member is a rod, of an oval, square, rectangular, triangular "C", "I" or "U" shaped cross section.

3. An apparatus, as claimed in claim 2, wherein said bore in the at least one buttress member is of complementary cross-section to said rod.

4. An apparatus, as claimed in claim 1, wherein the abutment surface of one or both of the buttress members is integrally provided with a plurality of conical-shaped spikes which are spaced apart from each other in positions inward from the outer perimeter of the one of both of the buttress members.

5. An apparatus, as claimed in claim 1, wherein one or both of said abutment surfaces includes a single lobe-shaped recess containing a bone growth promoter.

6. An apparatus, as claimed in claim 1, wherein one or both of said abutment surfaces is integrally provided with a plurality of conical-shaped spikes which are spaced apart from each other in positions inward from the outer perimeter of the one of both of the buttress members, and includes a single recess containing a bone growth promoter, the recess having a plurality of lobes equal in number to the plurality of spikes, the lobes extending radially between the spikes.

7. An apparatus, as claimed in claim 6, wherein one or both of said abutment surfaces includes a porous coating of one or more layers of spherical particles.

8. An apparatus, as claimed in claim 1, wherein said bore in the at least one of said buttress members is a blind passage.

9. A method for retaining vertebra of a spinal column in a desired spatial relationship, the method comprising:
    (a) excising portions of upper and lower vertebrae to form contact surfaces;
    (b) providing a spinal implant as claimed in any preceding claim;
    (c) installing said implant between said upper and lower vertebrae by placing said abutment surfaces in contact with said contact surfaces;
    (d) distracting said spinal column to adopt the desired spatial relationship of the vertebrae;
    (e) sliding at least one of said buttresses apart along said tensioning member such that said abutment surfaces maintain contact with said contact surfaces;
    (f) applying said retaining means to secure said buttresses to said tensioning member, to maintain said vertebrae in desired spatial relationship.

10. A method, as claimed in claim 9, wherein said buttresses and said tensioning member are of titanium or a titanium based alloy.

11. An apparatus, as claimed in claim 1, wherein since the tensioning member is adjustably connected with the at least one buttress member, the spacing between the buttress members is capable of being increased or decreased.

12. An apparatus, as claimed in claim 1, wherein the bore has a non-circular cross-section for receiving the one of the first and second ends of the tensioning member.

13. An apparatus, as claimed in claim 1, wherein the at least one buttress member includes a window opening extending in a radial direction, the window opening formed as a cylindrical bore extending radially from an outside of the at least one buttress member to the bore formed along the central axis, thus enabling a user of the apparatus to view the one of the first and second ends of the tensioning member which is slidably movable within the bore.

14. An apparatus, as claimed in claim 1, wherein each of the first and second buttress members includes the bore which opens from the end of the buttress member opposite from the abutment surface, and terminates at the closed inner end surface inside the respective buttress member,
    the bore of the first buttress member being adapted to receive and completely surround the first end of said tensioning member, and the bore of the second buttress member being adapted to receive and completely surround the second end of said tensioning member, and when the first and second ends of said tensioning member are contained, respectively, within the bores, the closed inner end surfaces prevent the ends of the tensioning members from projecting beyond the closed inner end surfaces.

* * * * *